(12) United States Patent
Chen et al.

(10) Patent No.: US 11,542,533 B2
(45) Date of Patent: Jan. 3, 2023

(54) METHOD FOR PRODUCING 1,3-PROPANEDIOL BY FERMENTATION OF A RECOMBINANT MICROORGANISM

(71) Applicant: TSINGHUA UNIVERSITY, Haidian District Beijing (CN)

(72) Inventors: Zhen Chen, Beijing (CN); Dehua Liu, Beijing (CN)

(73) Assignee: Tsinghua University, Beijing (CN)

( * ) Notice: Subject to any disclaimer, the term of this patent is extended or adjusted under 35 U.S.C. 154(b) by 152 days.

(21) Appl. No.: 16/957,081

(22) PCT Filed: Jul. 17, 2018

(86) PCT No.: PCT/CN2018/095893
§ 371 (c)(1),
(2) Date: Nov. 17, 2020

(87) PCT Pub. No.: WO2019/119789
PCT Pub. Date: Jun. 27, 2019

(65) Prior Publication Data
US 2021/0123079 A1    Apr. 29, 2021

(30) Foreign Application Priority Data
Dec. 22, 2017 (CN) .......................... 201711405440.5

(51) Int. Cl.
*C12N 1/16* (2006.01)
*C12N 1/20* (2006.01)
(Continued)

(52) U.S. Cl.
CPC .................. *C12P 7/18* (2013.01); *C12N 1/16* (2013.01); *C12N 1/20* (2013.01); *C12N 9/0006* (2013.01);
(Continued)

(58) Field of Classification Search
None
See application file for complete search history.

(56) References Cited

U.S. PATENT DOCUMENTS

2004/0197881 A1    10/2004    Park et al.
2012/0301935 A1    11/2012    Yu et al.
2021/0123079 A1*    4/2021    Chen .................... C12N 9/0008

FOREIGN PATENT DOCUMENTS

CN    106906248 A    6/2017
CN    107400652 A    11/2017
(Continued)

OTHER PUBLICATIONS

Office Action issued in corresponding Russian Application No. 2020124095 dated Feb. 26, 2021.
(Continued)

*Primary Examiner* — Richard C Ekstrom
(74) *Attorney, Agent, or Firm* — Saul Ewing LLP; Sean P. Ritchie

(57) ABSTRACT

Provided is a method for producing 1,3-propanediol by means of fermentation of a recombinant microorganism. First, a recombinant microorganism is provided; the recombinant microorganism can overexpress acetyl-CoA carboxylase genes: accBC and accDA, a malonyl-CoA synthetase gene: mcr, a 3-hydroxypropionyl-CoA synthetase gene: pcs, a 3-hydroxypropionyl-CoA reductase gene: pduP, and a 1,3-propanediol reductase gene: yqhD. The recombinant microorganism is subjected to fermentation culture in a flask or fermentor using glucose ad as raw material to obtain the 1,3-propanediol. The recombinant microorganism can utilize low-cost glucose, sucrose, molasses, xylose and the like as raw material in the fermentation process, without additional expensive vitamin B12. Thus, cost of the production
(Continued)

is significantly reduced, and there is a promising prospect in market.

8 Claims, 1 Drawing Sheet

Specification includes a Sequence Listing.

(51) Int. Cl.
 *C12P 7/18* (2006.01)
 *C12N 9/04* (2006.01)
 *C12N 9/88* (2006.01)
 *C12N 9/00* (2006.01)

(52) U.S. Cl.
 CPC .............. *C12N 9/88* (2013.01); *C12N 9/93* (2013.01); *C12Y 101/01202* (2013.01); *C12Y 402/01116* (2013.01); *C12Y 602/01036* (2013.01); *C12Y 604/00* (2013.01); *C12Y 604/01002* (2013.01)

(56) References Cited

FOREIGN PATENT DOCUMENTS

| CN | 108085288 A | 5/2018 |
| KR | 1020120099315 A | 10/2012 |
| RU | 2286330 C2 | 10/2006 |
| WO | WO 02/42418 A2 | 5/2002 |
| WO | WO03/029161 A1 | 4/2003 |
| WO | WO 2014/210535 A2 | 12/2014 |

OTHER PUBLICATIONS

Search report issued in corresponding Russian Application No. 2020124095.
Supplementary European Search Report dated Sep. 29, 2021.
Liang et al: Construction of stress-induced metabolic pathway from glucose to 1,3-propanediol in, Applied Microbiology and Biotechnology, vol. 89, No. 1, Aug. 28, 2010 (Aug. 28, 2010), pp. 57-62.
Eun-Hee S. et al: Development of microbial conversion process for production of 3-hydroxypropionic acid, May 1, 2015 (May 1, 2015), pp. 1-137.
Li Z. et al: Efficient Production of 1,3-Propanediol from Diverse Carbohydrates via a Non-natural Pathway Using 3-Hydroxypropionic Acid as an Intermediate, ACS Synthetic Biology, vol. 10, No. 3, Feb. 24, 2021 (Feb. 24, 2021), pp. 478-486.
Feng, et al., Recent Advances in Biosynthesis of 3-Hydroxypropionate, Biobuisness.com; 2017, pp. 30-43.
Lee, et al., Enhancement of 1,3-propanediol production by expression of pyruvate decarboxylase and aldehyde dehydrogenase from Zymomonas mobilis in the acetolactate-synthase-deficient mutant of Klebsiella pneumoniae, J Ind Microbiol Biotechnol (2014) 41:1259-1266.
Li, et al., Cloning and expression of 1,3-propenediol oxidoreductase isoenzyme gene yqhd from *Escherichia coli*, Chemical Industry and Engineering Progress, 2008, pp. 527-530.
International Search Report for PCT/CN2018/095893.

\* cited by examiner

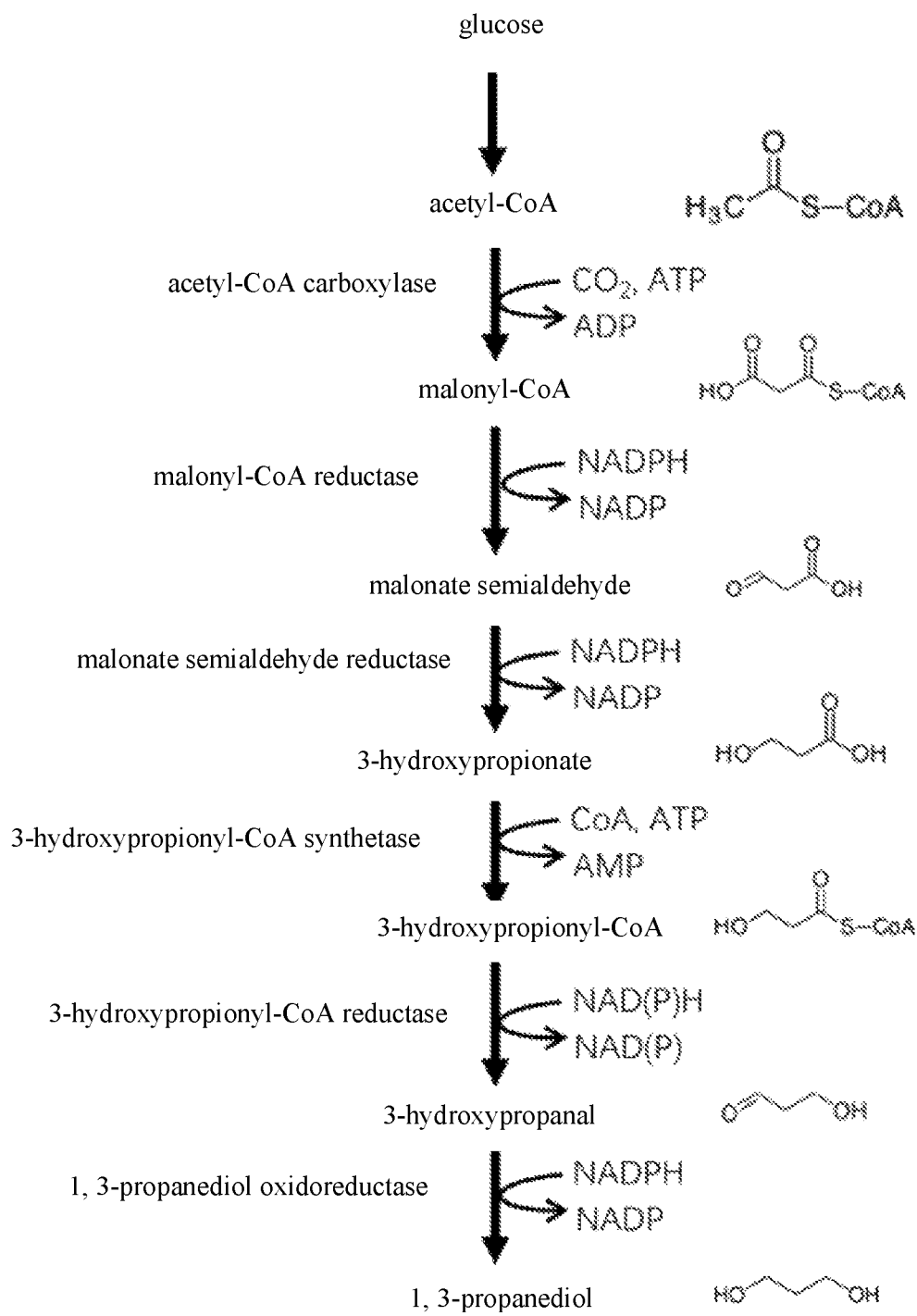

SEQUENCE LISTING

<160> NUMBER OF SEQ ID NOS: 18

<210> SEQ ID NO 1
<211> LENGTH: 1776
<212> TYPE: DNA
<213> ORGANISM: Artificial Sequence
<220> FEATURE:
<223> OTHER INFORMATION: accBC gene

<400> SEQUENCE: 1

| | | | | | |
|---|---|---|---|---|---|
| atgtcagtcg | agactaggaa | gatcaccaag | gttcttgtcg | ctaaccgtgg | tgagattgca | 60 |
| atccgcgtgt | tccgtgcagc | tcgagatgaa | ggcatcggat | ctgtcgccgt | ctacgcagag | 120 |
| ccagatgcag | atgcaccatt | cgtgtcatat | gcagacgagg | cttttgccct | cggtggccaa | 180 |
| acatccgctg | agtcctacct | tgtcattgac | aagatcatcg | atgcggcccg | caagtccggc | 240 |
| gccgacgcca | tccaccccgg | ctacggcttc | ctcgcagaaa | acgctgactt | cgcagaagca | 300 |
| gtcatcaacg | aaggcctgat | ctggattgga | ccttcacctg | agtccatccg | ctccctcggc | 360 |
| gacaaggtca | ccgctcgcca | catcgcagat | accgccaagg | ctccaatggc | tcctggcacc | 420 |
| aaggaaccag | taaaagacgc | agcagaagtt | gtggctttcg | ctgaagaatt | cggtctccca | 480 |
| atcgccatca | aggcagcttt | cggtggcggc | ggacgtggca | tgaaggttgc | ctacaagatg | 540 |
| gaagaagtcg | ctgacctctt | cgagtccgca | cccgtgaag | caaccgcagc | gttcggccgc | 600 |
| ggcgagtgct | tcgtggagcg | ctacctggac | aaggcacgcc | acgttgaggc | tcaggtcatc | 660 |
| gccgataagc | acggcaacgt | tgttgtcgcc | ggaacccgtg | actgctccct | gcagcgccgt | 720 |
| ttccagaagc | tcgtcgaaga | agcaccagca | ccattcctca | ccgatgacca | gcgcgagcgt | 780 |
| ctccactcct | ccgcgaaggc | tatctgtaag | gaagctggct | actacggtgc | aggcaccgtt | 840 |
| gagtacctcg | ttggctccga | cggcctgatc | tccttcctcg | aggtcaacac | ccgcctccag | 900 |
| gtggaacacc | cagtcaccga | agagaccacc | ggcatcgacc | tggtccgcga | aatgttccgc | 960 |
| atcgcagaag | gccacgagct | ctccatcaag | gaagatccag | ctccacgcgg | ccacgcattc | 1020 |
| gagttccgca | tcaacggcga | agacgctggc | tccaacttca | tgcctgcacc | aggcaagatc | 1080 |
| accagctacc | gcgagccaca | gggcccaggc | gtccgcatgg | actccggtgt | cgttgaaggt | 1140 |
| tccgaaatct | ccggacagtt | cgactccatg | ctggcaaagc | tgatcgtttg | gggcgacacc | 1200 |
| cgcgagcagg | ctctccagcg | ctcccgccgt | gcacttgcag | agtacgttgt | cgagggcatg | 1260 |
| ccaaccgtta | tcccattcca | ccagcacatc | gtggaaaacc | cagcattcgt | gggcaacgac | 1320 |
| gaaggcttcg | agatctacac | caagtggatc | gaagaggttt | gggataaccc | aatcgcacct | 1380 |
| tacgttgacg | cttccgagct | cgacgaagat | gaggacaaga | ccccagcaca | gaaggttgtt | 1440 |
| gtggagatca | acggccgtcg | cgttgaggtt | gcactcccag | gcgatctggc | actcggtggc | 1500 |
| accgctggtc | ctaagaagaa | ggccaagaag | cgtcgcgcag | gtggtgcaaa | ggctggcgta | 1560 |
| tccggcgatg | cagtggcagc | tccaatgcag | ggcactgtca | tcaaggtcaa | cgtcgaagaa | 1620 |
| ggcgctgaag | tcaacgaagg | cgacaccgtt | gttgtcctcg | aggctatgaa | gatggaaaac | 1680 |
| cctgtgaagg | ctcataagtc | cggaaccgta | accggcctta | ctgtcgctgc | aggcgagggt | 1740 |
| gtcaacaagg | gcgttgttct | cctcgagatc | aagtaa | | | 1776 |

<210> SEQ ID NO 2
<211> LENGTH: 1455
<212> TYPE: DNA
<213> ORGANISM: Artificial Sequence
<220> FEATURE:
<223> OTHER INFORMATION: accDA gene

<400> SEQUENCE: 2

```
atggtgtggg gcatggaaca cacttcagca ttgacgctca tagactcggt tttggaccct      60
gacagcttca tttcttggaa tgaaactccc caatatgaca acctcaatca aggctatgca     120
gagaccttgg agcgggctcg aagcaaggcc aaatgcgatg aatcggtaat tactggagaa     180
ggcaccgtgg agggcattcc ggtagccgtt attttgtccg attttccctt cctcggcggt     240
tctttgggca cggtcgcgtc ggtgcgcatc atgaaggcga ttcaccgcgc cacagagctg     300
aaactcccac tgctggtctc ccctgcttcc ggtggtgcgc gcatgcagga agacaatcga     360
gcttttgtca tgatggtgtc cataaccgcg gctgtgcagc gtcaccgcga ggcgcatttg     420
ccgttcctgg tgtatttgcg caatcccacg atgggtggcg ccatggcctc gtggggttca     480
tctgggcatc tcacttttgc ggaacccggc gcgcagatag gtttcctggg tcctcgcgtg     540
gtggagttaa ccactgggca tgcgcttcca gacggtgtgc agcaggcgga gaatttggtg     600
aaaactggtg tgattgatgg aattgtgtcg ccactccaat gcgtgcagc ggtggcaaaa      660
accctcaagg ttattcagcc ggtagaggca acggatcgtt tttctccaac aactcctggc     720
gtggcacttc cggtgatgga ggcgattgcg cgttctcgtg acccgcagag gcctggaatc     780
ggggagatta tggaaacgtt gggggcagac gtcgtcaagc tttctggtgc gcgtgctggc     840
gcattgagcc cggctgtgcg cgttgccctg gcgcgcatcg ggggccggcc cgtggtgctg     900
attgggcagg atcgccgctt cacgcttggg ccgcaggagc tgcgttttgc gcgtcgtggc     960
atttcgctgg cgcgcgagct aaacctgccg atcgtgtcca tcatcgacac ctccggcgcc    1020
gaattgtcgc aggcggctga ggagctcggc atcgcaagct cgattgcgcg caccttgtcc    1080
aagcttatcg acgctcccct ccccaccgtt tcggtcatta ttggtcaggg cgttggcggt    1140
ggcgcgctgg ccatgctgcc cgccgatctg gtctacgcgg ccgaaaacgc gtggctgtcc    1200
gcattgccac cagagggcgc ctcggccatc ctcttccgcg acaccaacca cgccgcggaa    1260
atcatagagc gacaaggcgt gcaggcgcac gcacttttaa gccaagggct tatcgacggg    1320
atcgtcgccg aaaccgagca ctttgttgaa gaaattctcg gcacaatcag caacgccctc    1380
tccgaattgg ataacaatcc ggagagggcg ggacgcgaca gtcgcttcac acgatttgag    1440
cgtttagcgc agtaa                                                     1455
```

<210> SEQ ID NO 3
<211> LENGTH: 3663
<212> TYPE: DNA
<213> ORGANISM: Artificial Sequence
<220> FEATURE:
<223> OTHER INFORMATION: mcr gene

<400> SEQUENCE: 3

```
atgtcgggca ctgggcgttt agccggtaaa atcgcgttga tcacgggcgg agcgggtaac      60
attggttctg aattgacgcg tcgcttttg gcggagggcg cgacggtcat catttctgga     120
cgcaaccgcg ccaaactgac ggcgttggct gagcgcatgc aagccgaagc aggagtgcct     180
gctaaacgca tcgatctgga agtcatggac ggttcggatc ccgtggcagt acgcgcgggt     240
atcgaagcaa ttgtagcacg ccacggacag attgatattt tagtcaacaa cgctggttcg     300
gcggggcgc agcgccgtct ggcagaaatc ccattaactg aggcagagtt agggcccggt     360
gcagaagaga ccttacatgc gtccattgct aacctgcttg gatgggctg cacttgatg      420
cgcatcgcgg ctccacacat gcctgtaggc tctgccgtga ttaatgtaag cacaatcttt    480
```

-continued

```
tcacgcgccg agtactatgg tcgtatccct tatgtaacgc caaaggcagc ccttaatgca    540
cttagtcagc ttgcggcgcg cgagttaggt gctcgtggca tccgtgtgaa tacgattttt    600
ccagggccaa ttgagtccga tcgcattcgt acggtgtttc agcgcatgga tcagttgaag    660
ggccgcccga aaggagacac agcacaccac tttctgaata ctatgcgcct ttgtcgtgcg    720
aacgaccaag gagctttgga acgccgtttc ccgagcgtcg gagacgtggc agatgctgcc    780
gtgttttttgg ccagtgccga gagtgctgcg cttttcgggag agactatcga ggtcactcac   840
ggtatggaac ttccagcgtg ctccgagaca tcacttctgg cacgtactga cttgcgtact    900
attgacgcgt caggccgtac taccctgatt tgcgcgggag atcaaattga agaggtcatg    960
gcgttgaccg gcatgctgcg cacatgtggg agtgaagtaa tcatcggatt ccgttccgca   1020
gcagcgttgg cgcagtttga acaggctgtt aacgaatccc gccgtttggc aggggctgac   1080
ttcactcctc ctatcgccct gccattagat ccacgtgatc cggctacaat cgatgcagtg   1140
ttcgattggg gtgcaggaga aaacacgggc gggatccacg ctgctgtaat cttaccggcg   1200
accagtcacg agcccgctcc ctgtgtcatc gaggtcgatg acgagcgtgt ccttaatttt   1260
ctggctgatg aaattacagg gaccattgta atcgcatctc gccttgcccg ttattggcaa   1320
agtcagcgtt tgacgcctgg tgcgcgtgcg cgcgggccac gtgtaatttt tctgtcgaat   1380
ggcgctgacc aaaatggcaa tgtgtacgga cgcattcaga gcgcagcaat tgggcaactt   1440
atccgtgtgt ggcgtcatga ggctgaattg gattatcagc gtgcaagtgc tgcggggat    1500
cacgttttac ctcccgtgtg ggcaaaccag attgttcgct ttgccaaccg tagtctggag   1560
ggtctggagt ttgcctgtgc ttggacggcg caacttctgc actcacagcg ccacattaac   1620
gagattactc tgaacatccc tgctaacatt ccgcgacca ccggcgcccg ttcggcttcg    1680
gtggggtggg cggaatcatt aatcgggctg catcttggta aggtggcgtt aattactgga   1740
ggtagcgccg gcattggagg gcaaattggg cgcctgcttg ctttatctgg ggcccgtgtg   1800
atgtggcgcg cgcgcgaccg tcataagctg aacagatgc aggctatgat tcagagcgag    1860
ttagccgaag tagggtatac cgacgttgaa gatcgcgtcc acattgcacc gggttgcgat   1920
gtatcaagcg aagctcaatt agccgattta gttgagcgca ccttgtccgc atttggtacc   1980
gtcgattatt taatcaataa tgcgggcatt gcgggcgtag aggagatggt tatcgacatg   2040
ccagtcgaag gctggcgcca cacgcttttt gcgaatctga tcagtaatta tagtttgatg   2100
cgcaaattag ctccgttaat gaagaagcaa ggatccggct acatcctgaa tgtatcatct   2160
tatttcggcg gagaaaaaga tgcggcgatt ccatacccga accgtgcgga ttacgctgta   2220
tcgaaggctg gtcaacgcgc tatggccgag gtatttgccc gtttcttagg tccagagatt   2280
cagatcaatg ccattgcacc aggccccgtt gagggcgatc gcttacgcgg gactggggag   2340
cgcccagggt tgtttgcgcg ccgcgcccgc cttatccttg agaataaacg cttaaacgaa   2400
ttgcacgcag ctcttatcgc cgctgccgc actgacgagc gtagcatgca cgagttagtg    2460
gaactgttgt taccaaacga tgttgctgcg ctggagcaga atcctgccgc tcccactgcc   2520
ttgcgtgaat tagcacgccg ttttcgtagc gaaggtgacc ctgctgcctc gtcgtcatcc   2580
gcccttctta accgctccat tgctgccaag ttgctggccc gttacacaa cggcgggtat    2640
gtgctgcccg ctgacatctt cgcgaatctg ccgaatccac ccgatccctt cttcacccgt   2700
gctcaaatcg accgcgaagc gcgcaaagtt cgcgatggta tcatgggcat gctgtacttg   2760
cagcgcatgc cgactgaatt tgatgtagcc atggcgaccg tgtactattt ggctgatcgc   2820
aacgtcagcg gagagaccct tcacccgtcc ggggattac gttatgagcg tactcctacg    2880
```

```
gggggagaat tgtttggcct gccttcacca gagcgccttg ccgaacttgt gggttcgact   2940
gtatacttaa tcggagaaca cttaactgaa catctgaatc tgctggcacg cgcatatctt   3000
gagcgttatg gagcgcgtca agtggtcatg attgtcgaaa ctgagaccgg tgccgagacg   3060
atgcgtcgtt tattcacgca ccacgtggaa gccggacgct taatgacaat cgtagctggg   3120
gatcaaatcg aagcagcaat cgaccaagcg attacccgtt acggtcgccc ggggccggtc   3180
gtgtgcaccc cttttcgtcc tcttcccact gtccctttag tagggcgtaa ggacagtgac   3240
tggagtaccg tgctttcaga agccgagttt gctgagttgt gcgagcatca attaacacat   3300
catttccgcg tagcccgtaa gatcgcgtta tcagatggtg catctttggc tcttgttact   3360
ccagaaacaa ctgctaccct ctacgaccgag cagtttgctt tggccaactt tattaagaca   3420
acattacatg ccttcacggc caccatcggc gttgagagcg aacgcaccgc tcagcgtatt   3480
ctgattaatc aggtggactt gactcgccgt gcgcgtgcgg aagagccgcg tgatccacat   3540
gagcgtcaac aagaattgga acgttttatt gaagcggttt tacttgttac agctcctctt   3600
cccccagagg ctgatactcg ctacgcgggt cgcattcacc gcggacgcgc aatcaccgtt   3660
taa                                                                3663

<210> SEQ ID NO 4
<211> LENGTH: 1986
<212> TYPE: DNA
<213> ORGANISM: Artificial Sequence
<220> FEATURE:
<223> OTHER INFORMATION: pcs gene

<400> SEQUENCE: 4 atgttttatgc gctacatcat ggtggaagag cagactttga aaactggaag ccaagagctt     60
gaagaaaaag ctgattataa tatgcgttac tacgcacacc ttatgaagct gtctaaagaa    120
aagcctgccg aatttggggg ctcttttggcg caagatcttc tggattggta tgagccctgg    180
aaggaaacga tgcgccaaga ggaccccatg acgcgctggt tcattggcgg aagattaat     240 gcgtcctaca atgctgtgga ccgtcatttg aacggccccc gcaaattcaa agctgcggta    300
atctgggaga gtgagttggg ggaacgtaaa atcgttactt accaagacat gttctacgaa    360
gtcaaccgct gggcaaacgc cttacgcagt cttggcgtag gtaaaggaga tcgcgtgacc    420
atttatatgc cgctgacccc agaaggaatc gcggccatgc tggcgtcagc tcgtattgga    480
gcgattcatt cagttatctt cgccggattt ggatcgcaag ccatcgccga ccgcgttgag    540
gacgccaagg caaagtcgt aatcaccgct gacgcatatc tcgtcgtgg taaagtagtt      600 gaactgaaaa agacagtgga cgaggccctt aattctttag gtgaacgtag tccagtgcaa    660
cacgtcctgg tctatcgccg catgaagaca acgttaaca tgaaagaagg gcgcgacgtt      720
ttcttcgacg aagtgggcaa ataccgctat gtggagcctg aacgtatgga ttctaacgac    780 cccttatta ttctgtacac gtcaggtact acaggtaaac caaggggat tatgcactcg      840 actggaggat atttgaccgg gacggcggtt atgctgcttt ggtcatatgg actgtcgcag    900
gagaatgatg tattattcaa tacttcagac atcggctgga tcgtgggtca ctcttacatc    960
acttactcgc cgttaatcat gggtcgcacg gtggtgatct atgagtctgc ccccgattac   1020
ccatatcccg ataagtgggc ggagatcatt gagcgttatc gcgctacaac ttttggtact   1080
tcagccacgg cgttgcgcta tttcatgaaa tacggggacg aatatgttaa gaatcatgat   1140
ttaagttcta ttcgtattat cgttacgaat ggcgaagttt tgaactatag ccctggaaa    1200
```

| | |
|---|---|
| tggggcttgg aagtgcttgg tggcggcaag gtattcatgt cgcatcaatg gtggcaaacg | 1260 |
| gagaccggag cacctaattt aggctacctg cctggcatta tttatatgcc gatgaaatct | 1320 |
| gggccagcgt ctggctttcc tctgcctgga aatttcgttg aagtccttga cgagaatggt | 1380 |
| aacccgagtg cgcctcgtgt acgtggctac cttgtaatgc gtccaccctt cccccaaac | 1440 |
| atgatgatgg gcatgtggaa tgacaacgga gagcgcctga agaaaactta tttctcaaaa | 1500 |
| tttggaagct tatactaccc cggagacttc gctatggttg atgaagacgg ttatatctgg | 1560 |
| gtactgggtc gtgcggacga acgttaaag atcgcggcac atcgtatcgg tgccggcgag | 1620 |
| gtcgaaagcg caatcacctc tcacccatca gttgcagaag ccgcagttat tggagttccg | 1680 |
| gattcagtga agggcgagga ggtgcatgcc ttcgtggttc tgaaacaagg gtacgctccg | 1740 |
| tcctctgagc ttgcaaagga cattcaaagt catgtccgta agtcatggg ccctattgta | 1800 |
| tcgccacaga ttcactttgt tgataaactt cctaagactc gctcgggtaa ggtgatgcgc | 1860 |
| cgtgtcatta aggccgtgat gatgggatcg tcggcaggcg accttaccac gattgaagac | 1920 |
| gaagcaagca tggatgaaat caagaaggcg gtggaagaac tgaagaagga attaaagact | 1980 |
| tcctaa | 1986 |

<210> SEQ ID NO 5
<211> LENGTH: 1389
<212> TYPE: DNA
<213> ORGANISM: Artificial Sequence
<220> FEATURE:
<223> OTHER INFORMATION: pduP gene

<400> SEQUENCE: 5

| | |
|---|---|
| atgaatacag cagaactgga aacccttatc cgcaccatcc tcagtgaaaa gctcgcgccg | 60 |
| acgcccctg cccctcagca agagcagggc attttctgcg atgtcggcag cgccatcgac | 120 |
| gccgctcatc aggctttct ccgctatcag cagtgtccgc taaaaacccg cagcgccatt | 180 |
| atcagcgccc tgcgggagac gctggccccc gagctggcga cgctggcgga agagagcgcc | 240 |
| acggaaaccg gcatgggcaa caaagaagat aaatatctga aaataaagc cgctcttgaa | 300 |
| aacacgccgg gcatagagga tctcactacc agcgccctca ccggcgatgg cgggatggtg | 360 |
| ctgtttgagt actcgccgtt cggggttatt ggcgccgtgg cgcccagcac caacccaacg | 420 |
| gaaaccatta tcaacaacag tatcagcatg ctggcggcgg gtaacagcgt ctatttcagc | 480 |
| ccccatcccg gcgcgaaaaa ggtctcgttg aagcttatcg ccaggatcga agagatcgcc | 540 |
| taccgctgca gcgggatccg taacctggtg gtgaccgttg ccgagccgac ctttgaagcc | 600 |
| acccagcaaa tgatgtccca cccgctgatt gccgttctgg ctatcaccgg cggccctggc | 660 |
| attgtggcga tggcatgaa aagcggtaaa aaagtgatcg gcgctggcgc cggcaatccg | 720 |
| ccgtgcatcg ttgatgaaac cgccgatctc gtcaaagccg ccgaagatat catcagcggc | 780 |
| gccgccttcg attacaacct gccctgtatc gccgaaaaaa gcctgatcgt cgtcgcctcc | 840 |
| gtcgctgacc gcctgatcca gcagatgcag gattttgacg cgctgctgtt gagccgacag | 900 |
| gaggccgata ccctgcgtgc cgtctgcctg cccgacggcg cggcgaataa aaaactggtc | 960 |
| ggtaaaagcc cggctcgcgct gctgcggcg gcgggtctcg ccgttccgcc tcgcccccct | 1020 |
| cgcctgctga tagccgaggt ggaggcgaac gaccctgg tgacctgcga gcagctgatg | 1080 |
| ccggtgctgc cgatcgtcag ggtgccgac tttgacagcg ccctggcgct ggccctgcgc | 1140 |
| gttgaggagg gtctgcacca caccgccatt atgcactcgc agaatgtctc gcggctcaat | 1200 |
| ctggcggcac gcacgctgca gacctccatt tttgtcaaaa atggcccgtc ttacgcggga | 1260 |

```
atcggcgtcg gcggcgaagg gtttaccacc ttcaccatcg ccacgccaac cggagaaggc    1320
accacctccg cgcggacgtt cgcccgcctg cggcgctgcg tgttgaccaa cggttttcc     1380 attcgctaa                                                             1389
```

<210> SEQ ID NO 6
<211> LENGTH: 1164
<212> TYPE: DNA
<213> ORGANISM: Artificial Sequence
<220> FEATURE:
<223> OTHER INFORMATION: yqhD gene

<400> SEQUENCE: 6

```
atgaacaact taatctgca caccccaacc cgcattctgt ttggtaaagg cgcaatcgct      60
ggtttacgcg aacaaattcc tcacgatgct cgcgtattga ttacctacgg cggcggcagc    120
gtgaaaaaaa ccggcgttct cgatcaagtt ctggatgccc tgaaaggcat ggacgtgctg    180
gaatttggcg gtattgagcc aaacccggct tatgaaacgc tgatgaacgc cgtgaaactg    240
gttcgcgaac agaaagtgac tttcctgctg gcggttggcg gcggttctgt actggacggc    300
accaaattta tcgccgcagc ggctaactat ccggaaaata tcgatccgtg gcacattctg    360
caaacgggcg gtaaagagat taaaagcgcc atcccgatgg gctgtgtgct gacgctgcca    420
gcaaccggtt cagaatccaa cgcaggcgcg gtgatctccc gtaaaaccac aggcgacaag    480
caggcgttcc attctgccca tgttcagccg gtatttgccg tgctcgatcc ggtttatacc    540
tacaccctgc cgccgcgtca ggtggctaac ggcgtagtgg acgcctttgt acacaccgtg    600
gaacagtatg ttaccaaacc ggttgatgcc aaaattcagg accgtttcgc agaaggcatt    660
ttgctgacgc taatcgaaga tggtccgaaa gccctgaaag agccagaaaa ctacgatgtg    720
cgcgccaacg tcatgtgggc ggcgactcag gcgctgaacg gtttgattgg cgctggcgta    780
ccgcaggact gggcaacgca tatgctgggc cacgaactga ctgcgatgca cggtctggat    840
cacgcgcaaa cactggctat cgtcctgcct gcactgtgga tgaaaaacg cgataccaag    900 cgcgctaagc tgctgcaata tgctgaacgc gtctggaaca tcactgaagg ttccgatgat    960
gagcgtattg acgccgcgat tgccgcaacc cgcaatttct ttgagcaatt aggcgtgccg   1020
acccacctct ccgactacgg tctggacggc agctccatcc cggctttgct gaaaaaactg   1080
gaagagcacg gcatgaccca actgggcgaa aatcatgaca ttacgttgga tgtcagccgc   1140
cgtatatacg aagccgcccg ctaa                                          1164
```

<210> SEQ ID NO 7
<211> LENGTH: 46
<212> TYPE: DNA
<213> ORGANISM: Artificial Sequence
<220> FEATURE:
<223> OTHER INFORMATION: primer accBC-F

<400> SEQUENCE: 7

```
tagcgcagta aaggagata taccatgtca gtcgagacta ggaaga                     46
```

<210> SEQ ID NO 8
<211> LENGTH: 47
<212> TYPE: DNA
<213> ORGANISM: Artificial Sequence
<220> FEATURE:
<223> OTHER INFORMATION: primer accBC-R

<400> SEQUENCE: 8
ctgcaggcgc gccgagctcg ttacttgatc tcgaggagaa caacgcc          47

<210> SEQ ID NO 9
<211> LENGTH: 44
<212> TYPE: DNA
<213> ORGANISM: Artificial Sequence
<220> FEATURE:
<223> OTHER INFORMATION: primer accDA-F

<400> SEQUENCE: 9
gtttaacttt aataaggaga tatacatggt gtggggcatg gaac             44

<210> SEQ ID NO 10
<211> LENGTH: 35
<212> TYPE: DNA
<213> ORGANISM: Artificial Sequence
<220> FEATURE:
<223> OTHER INFORMATION: primer accDA-R

<400> SEQUENCE: 10
tatatctcct tttactgcgc taaacgctca aatcg                       35

<210> SEQ ID NO 11
<211> LENGTH: 47
<212> TYPE: DNA
<213> ORGANISM: Artificial Sequence
<220> FEATURE:
<223> OTHER INFORMATION: primer mcr-F

<400> SEQUENCE: 11
gcgatcgctg acgtcggtac aaggagatat acatatgtcg ggcactg          47

<210> SEQ ID NO 12
<211> LENGTH: 41
<212> TYPE: DNA
<213> ORGANISM: Artificial Sequence
<220> FEATURE:
<223> OTHER INFORMATION: primer mcr-R

<400> SEQUENCE: 12
tttaccagac tcgagggtac ttaaacggtg attgcgcgtc c                41

<210> SEQ ID NO 13
<211> LENGTH: 48
<212> TYPE: DNA
<213> ORGANISM: Artificial Sequence
<220> FEATURE:
<223> OTHER INFORMATION: primer pcs-F

<400> SEQUENCE: 13
ctttaagaag gagatatacc aggaggaaac agaaccatgt ttatgcgc         48

<210> SEQ ID NO 14
<211> LENGTH: 46
<212> TYPE: DNA
<213> ORGANISM: Artificial Sequence
<220> FEATURE:
<223> OTHER INFORMATION: primer pcs-R

<400> SEQUENCE: 14
acgttaatgg ttaggaagtc tttaattcct tcttcagttc ttccac           46

<210> SEQ ID NO 15

```
<211> LENGTH: 42
<212> TYPE: DNA
<213> ORGANISM: Artificial Sequence
<220> FEATURE:
<223> OTHER INFORMATION: primer pduP-F

<400> SEQUENCE: 15
gacttcctaa ccattaacgt gagaactcat caatgaatac ag                          42

<210> SEQ ID NO 16
<211> LENGTH: 49
<212> TYPE: DNA
<213> ORGANISM: Artificial Sequence
<220> FEATURE:
<223> OTHER INFORMATION: primer pduP-R

<400> SEQUENCE: 16
atatgtatat ctccttctta aagttttagc gaatggaaaa accgttggt                   49

<210> SEQ ID NO 17
<211> LENGTH: 42
<212> TYPE: DNA
<213> ORGANISM: Artificial Sequence
<220> FEATURE:
<223> OTHER INFORMATION: primer yqhD-F

<400> SEQUENCE: 17
taagaaggag atatacatat gaacaacttt aatctgcaca cc                          42

<210> SEQ ID NO 18
<211> LENGTH: 41
<212> TYPE: DNA
<213> ORGANISM: Artificial Sequence
<220> FEATURE:
<223> OTHER INFORMATION: primer yqhD-R

<400> SEQUENCE: 18
caagcttgtc gacggagctc gcgggcggct tcgtatatac g                           41
```

METHOD FOR PRODUCING 1,3-PROPANEDIOL BY FERMENTATION OF A RECOMBINANT MICROORGANISM

RELATED APPLICATIONS

This application is a national stage application claiming priority from International Patent Application No. PCT/CN2018/095893, filed Jul. 17, 2018, which claims the benefit of CN Patent Application No. 201711405440.5, filed Dec. 22, 2017, the entire disclosures of which are incorporated herein by this reference.

SEQUENCE LISTING

The instant application contains a Sequence Listing which has been submitted in ASCII format via EFS-Web and is hereby incorporated by reference in its entirety. The ASCII copy of the Sequence Listing, which was created on Oct. 19, 2020, is named NT012N-2020589.txt and is 18.0 kilobytes in size.

FIELD OF THE INVENTION

The invention relates to the field of genetic engineering or biological fermentation, in particular a method of efficiently bio-converting a fermentable carbohydrate to 1,3-propanediol by using a single recombinant microorganism without addition of vitamin B12.

PRIOR ART 1,3-propanediol, an important chemical raw material, may be used as an organic solvent in many industries, such as ink industry, printing and dyeing industry, painting industry, lubricant industry, and/or antifreeze industry. The main usage of 1,3-propanediol is that it can be used as a monomer for synthesizing polyester and polyurethane. In particular, 1,3-propanediol can be used to produce polytrimethylene terephthalate (PTT) by polymerizing with terephthalic acid. Compared with polyethylene terephthalate (PET), or polybutylene terephthalate (PBT), the PTT shows better performance in many aspects, such as better pollution resistance, toughness, re-bouncing and ultraviolet resistance, as well as wear resistance, low water absorption, and/or low static electricity. Thus, PTT is considered as an upgraded product of the PET, and has a promising prospect in commercial market.

At present, methods for producing 1,3-propanediol basically include chemical methods and biological methods. By the chemical methods, 1,3-propanediol can be synthesized through a complicated catalytic process by using propylene oxide or propylene as raw material. Disadvantages of the chemical methods include excessive by-products, poor selectivity, high temperature and pressure of operation condition, vast investment of equipments, and non-renewability of raw materials. Thus, the technical process adopting the chemical methods for producing 1,3-propanediol has been abandoned.

The biological methods for producing 1,3-propanediol include two main technical protocols: one is to produce 1,3-propanediol with a natural microorganism using glycerin as the raw material, and the other is to produce 1,3-propanediol with a recombinant microorganism by using glucose as the raw material. Both are described as below.

In one technical protocol, 1,3-propanediol is produced using glycerin as the raw material by a natural microorganism such as *Klebsiella pneumoniae, Clostridium butyricum*, or *Citrobacter freundii* which can convert glycerin into 1,3-propanediol under anaerobic or microaerobic conditions. The disadvantages of the technical protocol mainly include that: 1. a strict regulation on bio-safety is required during the production, because *Klebsiella pneumoniae* which is commonly employed is a conditioned pathogen; 2. the synthesis of many by-products, such as acetic acid, lactic acid, succinic acid and 2,3-butanediol renders later extraction processes very complicated; and 3. the price of glycerin fluctuates dramatically in commercial market.

There is another method in the prior art of producing 1,3-propanediol by using glucose as the raw material with a recombinant microorganism. For example, DuPont realizes one step conversion of glucose to 1,3-propanediol by exogenously expressing the glycerol synthesis pathway (the glycerol 3-phosphate dehydrogenase and the glycerol 3-phosphotase) from *Saccharomyces cerevisiae* as well as the glycerol dehydratase and its activating factors from *Klebsiella pneumoniae* in *E. coli* together with the NADPH-depended alcohol dehydrogenase, YqhD from *E. coli* (CN 200380104657.2). The disadvantage of this process is that the glycerol dehydratase requires the coenzyme B12 as co-factor which however cannot be synthesized by *E. coli*, so that the expensive vitamin B12 requires to be added during the fermentation, which dramatically increases the production cost and is not favorable for industrial and large-scale production.

DISCLOSURE OF THE INVENTION

The purpose of the invention is to provide a new method of directly converting a fermentable carbohydrate to 1,3-propanediol using a recombinant microorganism, which is of low cost and does not require the expensive vitamin B12 to be added.

Firstly, the invention provides a recombinant microorganism capable of overexpressing:
(1) the acetyl-CoA carboxylase genes accBC and accDA;
(2) the malonyl-CoA synthetase gene mcr;
(3) the 3-hydroxypropionyl-CoA synthetase gene pcs;
(4) the 3-hydroxypropionyl-CoA reductase gene pduP; and
(5) the 1,3-propanediol oxidoreductase gene yqhD.

A person skilled in the art will understand that: the microorganism according to the invention may be conventional model microorganisms, including but not limited to *E. coli, Corynebacterium glutamicum, Bacillus subtilis*, or *Saccharomyces cerevisiae*.

The recombinant microorganism according to the invention can express the acetyl-CoA carboxylase genes accBC and accDA, whose nucleotide sequences are set forth in SEQ ID Nos: 1 and 2, respectively.

In the examples of the invention, the acetyl-CoA carboxylase genes accBC and accDA are from *Corynebacterium glutamicum*.

Further, the recombinant microorganism according to the invention can express the malonyl-CoA synthetase gene mcr whose nucleotide sequence is set forth in SEQ ID NO: 3. In the examples of the invention, the malonyl-CoA synthetase gene mcr is from *Chloroflexus aurantiacus*.

Furthermore, the recombinant microorganism according to the invention can express the 3-hydroxypropionyl-CoA synthetase gene pcs, the 3-hydroxypropionyl-CoA reductase gene pduP, and the 1,3-propanediol oxidoreductase gene yqhD. In the examples of the invention, the 3-hydroxypropionyl-CoA synthetase gene pcs is from *Metallosphaera*

*sedula*, whose nucleotide sequence is set forth in SEQ ID NO: 4; the 3-hydroxypropionyl-CoA reductase gene pduP is from *Klebsiella pneumoniae*, whose nucleotide sequence is set forth in SEQ ID NO: 5; and the 1,3-propanediol oxidoreductase gene yqhD is from *E. coli*, whose nucleotide sequence is set forth in SEQ ID NO: 6. A person skilled in the art will understand that the description is not limited to the enzymes of the strains in the examples, and that any enzyme from other sources which shows the same function can also achieve the same the technical effects.

In the examples of the invention, the recombinant microorganism was obtained by the following processes:

(1) linking the gene accBC the sequence of which is set forth in SEQ ID NO: 1, and the gene accDA the sequence of which is set forth in SEQ ID NO: 2 to the plasmid pACYCDuet, to obtain the recombinant plasmid pACYC-accDABC;

(2) linking the mcr fragment of 3.7 kb obtained by PCR amplification using the nucleotide sequence of SEQ ID NO: 3 as a template, with the primers set forth in SEQ ID NOs: 11-12, to the plasmid pACYC-accDABC, to obtain the recombinant plasmid pACYC-accDABC-mcr, and then transforming this recombinant plasmid into *E. coli* to obtain the recombinant strain, *E. coli*/pACYC-accDABC-mcr after screening;

(3) linking the pcs fragment of 2.0 kb obtained by PCR amplification using the nucleotide sequence of SEQ ID NO: 4 as a template, with the primers set forth in SEQ ID NOs:13-14, the pduP fragment of SEQ ID NO: 5, and the yqhD fragment of SEQ ID NO: 6 to the plasmid pET28, to obtain the recombinant plasmid pET-pcs-pduP-yqhD;

(4) transforming the pET-pcs-pduP-yqhD into the recombinant strain *E. coli*/pACYC-accDABC-mcr obtained in the step (2), to obtain the recombinant strain *E. coli*/pACYC-accDABC-mcr/pET-pcs-pduP-yqhD after screening, which is the recombinant microorganism according to the invention.

The invention provides use of the recombinant microorganism in the production of 1,3-propanediol.

The invention provides a method of producing 1,3-propanediol by fermentation with the recombinant microorganism, comprising the steps of:

(1) constructing the recombinant microorganism capable of overexpressing the acetyl-CoA carboxylase genes accBC and accDA, the malonyl-CoA synthetase gene mcr, the 3-hydroxypropionyl-CoA synthetase gene pcs, the 3-hydroxypropionyl-CoA reductase gene pduP, and the 1,3-propanediol oxidoreductase gene yqhD; and (2) conducting an aerobic fermentation using a raw material comprising a fermentable carbohydrate as the substrate and without the need of adding the vitamin B12.

The raw material comprising a fermentable carbohydrate in the step (2) is molasses, sucrose, glucose, starch hydrolysate, corn syrup, xylose, mannose, or glycerin.

The conditions for fermentation in the step (2) are: 28° C. to 37° C., a pH value in a range from 5 to 8, and a dissolved oxygen value greater than 10%.

Preferably, the fermentation conditions in the step (2) are: 30° C. to 37° C., a pH value in a range from 6 to 7, and the dissolved oxygen value greater than 10%.

The substrate for fermentation in the step (2) further comprises $Na_2HPO_4$, $KH_2PO_4$, $MgSO_4$, NaCl, yeast extract, $NH_4Cl$, thiamine hydrochloride, and biotin.

The invention proposed a synthesis pathway of 1,3-propanediol as shown in FIG. 1: firstly, the acetyl-CoA is generated from glucose (or another fermentable carbohydrate) through the glycolysis pathway in the microorganism itself; the acetyl-CoA generates the malonyl-CoA under the catalysis of the acetyl-CoA carboxylase; the malonyl-CoA generates malonate semialdehyde under the catalysis of the malonyl-CoA reductase; the malonate semialdehyde produces 3-hydroxypropionate under the catalysis of the malonate semialdehyde reductase; the 3-hydroxypropionate produces the 3-hydroxypropionyl CoA under the catalysis of the 3-hydroxypropionyl coenzyme A synthase; the 3-hydroxypropionyl CoA produces 3-hydroxypropanal under the catalysis of the 3-hydroxypropionyl CoA reductase; and the 3-hydroxypropanal produces 1,3-propanediol under the catalysis of the 1,3-propanediol oxidoreductase.

According to the invention, 1,3-propanediol is produced through fermentation in a flask or a fermenter using glucose as substrate, by a recombinant microorganism capable of overexpressing the acetyl-CoA carboxylase genes accBC and accDA, the malonyl-CoA synthetase gene mcr, the 3-hydroxypropionyl-CoA synthetase gene pcs, the 3-hydroxypropionyl-CoA reductase gene pduP, and the 1,3-propanediol oxidoreductase gene yqhD. During the fermentation process, the recombinant microorganism according to the invention can use the cheap glucose as the raw material without the need of adding the expensive vitamin B12, which could lower production cost dramatically, and has a promising prospect in commercial market. The method according to the invention is simplified, of low cost, produces a high yield of 1,3-propanediol with fewer by-products, and is beneficial for simplifying the separation of 1,3-propanediol.

BRIEF DESCRIPTION OF THE FIGURES

FIG. 1 is a flowchart relating to the method for producing 1,3-propanediol using glucose by fermentation with a recombinant microorganism according to the invention.

DETAILED DESCRIPTION OF THE INVENTION

The examples below are only used to illustrate the invention, but not intended to limit the scope of the invention. Without deviating the spirit and essence of the invention, any amendment and replacement with respect to the method, step or condition of the invention also fall within the scope of the invention.

Unless indicated otherwise, chemical reagents used in the examples are conventional commercially available, and techniques used in the examples are conventional to a person skilled in the art.

Example 1

Construction of a recombinant plasmid for overexpressing the acetyl-CoA carboxylase genes accBC and accDA.

The gene accBC (the nucleotide sequence of which is set forth in SEQ ID NO: 1) of about 1.8 Kb was obtained by PCR amplification using the genome of *Corynebacterium glutamicum* ATCC 13032 as a template, with the primers accBC-F (tagcgcagtaaAAGGAGATATACCatgt cagtcgagactaggaaga) and accBC-R (CTGCAGGCGCGCCGAGCTCGttacttgatctcgaggagaaca acgcc) and purified.

The gene accDA (the nucleotide sequence of which is set forth in SEQ ID NO: 2) of about 1.5 kb was obtained by PCR amplification using the genome of *Corynebacterium glutamicum* ATCC 13032 as a template, with the primers accDA-F (GTTTAACTTTAATAAGGAGATATACatggtgtggggcatggaac) and accDA-R (TATATCTCCTTttactgcgctaaacgctcaaatcg) and purified. The plasmid pACYCDuet (Novagen) was cleaved with NcoI and EcoRI; and the purified accBC and accDA fragments were one-step linked into the pACYCDuet by using the Gibson Assembly Kit (NEB), to obtain a recombinant plasmid designated as pACYC-accDABC.

Example 2

Construction of a recombinant plasmid for overexpressing the malonyl-CoA synthetase gene mcr.

Based on the amino acid sequence of the malonyl-CoA synthetase from *Chloroflexus aurantiacus*, an optimized nucleic acid sequence of the gene was artificially designed (the gene sequence is set forth in SEQ ID NO: 3) and synthesized by the Qinglan Biotech. Inc. A mcr fragment of about 3.7 kb was obtained by PCR using the gene fragment as a template with the primers mcr-F (GC-GATCGCTGACGTCGGTACAAGGAGATATA-CATATGTCGGGC ACTG) and mcr-R (TTTACCA-GACTCGAGGGTACTTAAACGGTGATTGCGCGTCC), and purified. The plasmid pACYC-accDABC prepared in the example 1 was cleaved with KpnI, the mcr fragment was one-step linked to the pACYC-accDABC using the Gibson Assembly Kit (NEB), to obtain the recombinant plasmid pACYC-accDABC-mcr. After transforming the pACYC-accDABC-mcr into *E. coli* BL21 (DE3) by thermal transformation, a recombinant microorganism was selected in a LB plate containing chloramphenicol of 25 mg/L, which was designated as *E. coli*/pACYC-accDABC-mcr.

Example 3

Construction of a recombinant plasmid for overexpressing the 3-hydroxypropionyl-CoA synthetase gene pcs, the 3-hydroxypropionyl-CoA reductase gene pduP, and the 1,3-propanediol oxidoreductase gene yqhD.

Based on the amino acid sequence of the 3-hydroxypropionyl-CoA synthetase from *Metallosphaera sedula*, an optimized nucleic acid sequence of the gene was artificially designed (the gene sequence is set forth in SEQ ID NO: 4) and synthesized by the Qinglan Biotech. Inc. A pcs fragment of about 2.0 kb was obtained by PCR using the gene fragment as a template, with the primers pcs-F (CTT-TAAGAAGGAGATATACCaggaggaaacagaaccATG TTTATGCGC) and pcs-R (acgttaatggTTAGGAAGTCTT-TAATTCCTTCTTCAGTTCTTCC AC) and purified. A pduP gene of about 1.5 kb (the nucleotide sequence of which is set forth in SEQ ID NO: 5) was obtained by PCR using the genome of *Klebsiella pneumoniae* DSM2026 as a template, with the primers pduP-F (GACTTCCTAAccattaacgt-gagaa ctcatcaatgaatacag) and pduP-R (atATGTATATCTCCTTCTTAAAGTTttagcgaatg-gaaaaaccgtt ggt), and purified. A yqhD gene of about 1.2 kb (the nucleotide sequence of which is set forth in SEQ ID NO: 6) was obtained by PCR using the genome of *E. coli* W3110 as a template, with the primers yqhD-F (TAAGAAGGAGATATACATatgAACAACTT-TAATCTGCACACC) and yqhD-R (CAAGCTTGTCGACG-GAGCTCGCGGGCGGCTTCGTATATACG), and purified. The plasmid pET32a (Novagen) was cleaved with NcoI and EcoRI, and the pcs fragment, the pduP fragment and the yqhD fragment were one-step linked into the pET28a to obtain a recombinant plasmid designated as pET-pcs-pduP-yqhD. After transforming the pET-pcs-pduP-yqhD into the *E. coli*/pACYC-accDABC-mcr obtained in the example 2 by thermal transformation, a recombinant microorganism was selected in a LB plate with Kanamycin at 25 mg/L and chloramphenicol at 25 mg/L, designated as *E. coli*/pACYC-accDABC-mcr/pET-pcs-pduP-yqhD.

Example 4

Production of 1,3-propanediol by fermentation with the recombinant *E. coli*

After culturing the *E. coli*/pACYC-accDABC-mcr/pET-pcs-pduP-yqhD obtained in the example 3 in a LB plate with Kanamycin (25 mg/L) and chloramphenicol (25 mg/L) overnight, a single colony from this fresh plate was inoculated to a 250 ml flask with baffle containing 30 ml seed culture medium, and incubated for 16 h at 30° C. and 200 rpm.

The composition of the seed culture medium comprises (g/L): glucose of 20, yeast extract of 5.0, peptone of 10, NaCl of 5.0, chloramphenicol of 0.025, and kanamycin of 0.025.

The seed broth was inoculated to a 1000 ml flask with baffle containing 100 ml fermentation culture medium at an inoculation amount of 10%, and incubated at 30° C. and 200 rpm. IPTG (0.5 mM) was added 6 hours after fermentation for induction and the fermentation were conducted for another 48 h.

The composition of the fermentation culture medium comprises (g/L): glucose of 20, $Na_2HPO_4 \cdot 7H_2O$ of 12.8, $K_2HPO_4$ of 3.0, $MgSO_4$ of 0.5, NaCl of 0.5, $NH_4Cl$ of 0.5, yeast extract of 10, biotin of 0.001, thiamine hydrochloride of 0.001, chloramphenicol of 0.025, and Kanamycin of 0.025.

The *E. coli*/pACYC-accDABC-mcr/pET-pcs-pduP-yqhD obtained in the example 3 was detected at 24 h after fermentation for the enzyme activities of the acetyl-CoA carboxylase, malonyl-CoA synthetase, 3-hydroxypropionyl-CoA synthetase, 3-hydroxypropionyl-CoA reductase and 1,3-propanediol oxidoreductase, which were 0.24 U/mg, 0.12 U/mg, 0.38 U/mg, 0.97 U/mg and 1.72 U/mg, respectively, indicating that each of the recombinant enzymes was expressed normally. Substantially no corresponding enzyme activities were detected in the control wildtype *E. coli* BL21 (DE3).

At 48 h after the fermentation, the *E. coli*/pACYC-accDABC-mcr/pET-pcs-pduP-yqhD obtained in the example 3 could produce 1,3-propanediol at 2.1 g/L, with a mass conversion rate of 0.105 g/g of glucose, showing that the constructed recombinant strain can convert glucose to 1,3-propanediol directly, without addition of the coenzyme B12. In the control experiment under the same conditions, both the wildtype *E. coli* BL21 (DE3) and the *E. coli*/pACYC-accDABC-mcr obtained in the example 2 could not produce 1,3-propanediol.

Although the general description and the embodiments above have described the invention in detail, it is apparent for a person skilled in the art to make modification or alteration to them based on the disclosure of the invention. Thus, such modification and alteration without departure of the spirit of the invention fall within the scope of the invention.

The invention claimed is:

1. A recombinant microorganism, characterized in that the recombinant microorganism is capable of overexpressing:
    (1) the acetyl-CoA carboxylase genes accBC and accDA;
    (2) the malonyl-CoA synthetase gene mcr;
    (3) the 3-hydroxypropionyl-CoA synthetase gene pcs;
    (4) the 3-hydroxypropionyl-CoA reductase gene pduP; and
    (5) the 1,3-propanediol oxidoreductase gene yqhD;
    wherein the nucleotide sequence of the 3-hydroxypropionyl-CoA synthetase gene pcs is set forth in SEQ ID NO: 4, and the nucleotide sequence of the 3-hydroxypropionyl-CoA reductase gene pduP is set forth in SEQ ID NO: 5.

2. The recombinant microorganism according to claim 1, characterized in that it is E. coli, Corynebacterium glutamicum, Bacillus subtilis, or Saccharomyces cerevisiae.

3. The recombinant microorganism according to claim 1, characterized in that the nucleotide sequences of the accBC and accDA are set forth in SEQ ID NOs: 1-2.

4. The recombinant microorganism according to claim 1, characterized in that the nucleotide sequence of the malonyl-CoA synthetase gene mcr is set forth in SEQ ID NO: 3.

5. The recombinant microorganism according to claim 1, characterized in that the nucleotide sequence of the 1,3-propanediol oxidoreductase gene yqhD is set forth in SEQ ID NO: 6.

6. Use of the recombinant microorganism according to claim 1 in the production of 1,3-propanediol by fermentation with a carbohydrate.

7. A method of producing 1,3-propanediol by using the recombinant microorganism according to claim 1, characterized in that it comprises steps of:
    (1) constructing a recombinant microorganism capable of overexpressing the acetyl-CoA carboxylase genes accBC and accDA, the malonyl-CoA synthetase gene mcr, the 3-hydroxypropionyl-CoA synthetase gene pcs, the 3-hydroxypropionyl-CoA reductase gene pduP and the 1,3-propanediol oxidoreductase gene yqhD; and
    (2) conducting an aerobic fermentation by using a raw material comprising a fermentable carbohydrate as substrate, without the need of adding coenzyme vitamin B12.

8. The method according to claim 7, characterized in that the raw material comprising a fermentable carbohydrate in the step (2) is molasses, sucrose, glucose, starch hydrolysate, corn syrup, xylose, mannose or glycerin; and conditions for fermentation are: 28° C. to 37° C., a pH value in a range from 5 to 8, and a dissolved oxygen value greater than 10%.

* * * * *